(12) United States Patent
Schroeder

(10) Patent No.: US 10,626,164 B2
(45) Date of Patent: Apr. 21, 2020

(54) PURIFICATION OF VWF

(71) Applicant: CSL Limited, Parkville (AU)

(72) Inventor: Magnus Schroeder, Parkville (AU)

(73) Assignee: CSL Limited, Parkville (AU)

( * ) Notice: Subject to any disclaimer, the term of this patent is extended or adjusted under 35 U.S.C. 154(b) by 231 days.

(21) Appl. No.: 14/805,351

(22) Filed: Jul. 21, 2015

(65) Prior Publication Data

US 2016/0024180 A1 Jan. 28, 2016

(30) Foreign Application Priority Data

Jul. 25, 2014 (AU) ................ 2014902892

(51) Int. Cl.
- C07K 14/745 (2006.01)
- C07K 1/16 (2006.01)
- C07K 14/755 (2006.01)

(52) U.S. Cl.
CPC ........ C07K 14/755 (2013.01); *C07K 2319/31* (2013.01)

(58) Field of Classification Search
None
See application file for complete search history.

(56) References Cited

U.S. PATENT DOCUMENTS

| | | | | |
|---|---|---|---|---|
| 5,869,617 A | * | 2/1999 | Fischer | C07K 14/755 530/381 |
| 8,329,871 B2 | * | 12/2012 | Borgvall | C07K 14/755 424/520 |
| 2012/0289468 A1 | * | 11/2012 | Barnett | C07K 14/755 514/14.1 |
| 2016/0024180 A1 | | 1/2016 | Schroeder et al. | |

FOREIGN PATENT DOCUMENTS

| | | |
|---|---|---|
| EP | 0503991 A1 | 9/1992 |
| EP | 0784632 B1 | 1/1999 |
| WO | WO 2009/131526 A1 | 10/2009 |
| WO | WO 2009/156137 A1 | 12/2009 |
| WO | WO 2011/060242 A2 | 5/2011 |
| WO | WO 2013/083858 A1 | 6/2013 |
| WO | WO 2013/106787 A1 | 7/2013 |

OTHER PUBLICATIONS

Burnouf-Radosevich, M., et al. 1992 Vox Sang 62: 1-11. (Year: 1992).*
GE Healthcare Life Sciences Multimodal Chromatography Handbook: 115 pages (Year: 2013).*
[Author Unknown], Capto™ Core 700, Data file 28-9983-07 AA, GE Healthcare Life Sciences, Multimodal Chromatography data sheet (Mar. 2012); pp. 1-4, 4 pages.
Burnouf-Radosevich and Burnouf, "Chromatographic Preparation of a Therapeutic Highly Purified von Willebrand Factor Concentrate from Human Cryoprecipitate." Vox Sanguinis (1992); 62: 1-11.
Collins, et al., "Molecular cloning of the human gene for von Willebrand factor and identification of the transcription initiation site." Proc. Natl. Acad. Sci. USA (1987); 84 (13): 4393-4397.
Fischer, et al., "Structural analysis of recombinant von Willebrand factor: identification of hetero- and homo-dimers." FEBS Letters (1994); 351 (3): 345-348.
Schulte, "Innovative coagulation factors: albumin fusion technology and recombinant single-chain factor VIII." Thrombosis Research (2013); 131 (S2): S2-S6.
Vergauwe et al., "Shear-Stress-Induced Conformational Changes of von Willebrand Factor in a Water—Glycerol Mixture Observed with Single Molecule Microscopy," J. Phys. Chem. B 2014, 118, 5660-5669.

* cited by examiner

*Primary Examiner* — Marsha Tsay

(57) ABSTRACT

The present invention provides a method of purifying multimeric von Willebrand Factor (VWF) from a solution comprising multimeric VWF and contaminants. The method comprises passing the solution through a chromatography column comprising beads of a mixed mode chromatography resin coated with a size-exclusion inactive shell and collecting the multimeric VWF which passes through the column without binding to the resin.

10 Claims, 2 Drawing Sheets

PURIFICATION OF VWF

CROSS REFERENCE TO RELATED APPLICATION

This application claims priority to Australian Patent Application No. AU2014902892, which is herein incorporated by reference in its entirety.

FIELD OF THE INVENTION

The present invention relates to a method of purifying von Willebrand Factor (VWF) using mixed mode chromatography.

BACKGROUND OF THE INVENTION

There are various bleeding disorders caused by deficiencies of blood coagulation factors. The most common disorders are hemophilia A and B, resulting from deficiencies of blood coagulation factor VIII and IX, respectively. Another known bleeding disorder is von Willebrand's disease.

VWF, which is missing, functionally defective or only available in reduced quantity in different forms of von Willebrand disease (VWD), is a multimeric adhesive glycoprotein present in plasma, which has multiple physiological functions. During primary hemostasis VWF acts as a mediator between specific receptors on the platelet surface and components of the extracellular matrix such as collagen. Moreover, VWF serves as a carrier and stabilizing protein for procoagulant FVIII. VWF is synthesized in endothelial cells and megakaryocytes as a 2813 amino acid precursor molecule.

The amino acid sequence and the cDNA sequence of wild-type VWF are disclosed in Collins et al. 1987, Proc Natl. Acad. Sci. USA 84:4393-4397. The precursor polypeptide, pre-pro-VWF, consists of a 22-residue signal peptide, a 741-residue pro-peptide and the 2050-residue polypeptide found in plasma (Fischer et al., FEBS Lett. 351: 345-348, 1994). After cleavage of the signal peptide in the endoplasmatic reticulum a C-terminal disulfide bridge is formed between two monomers of VWF. During further transport through the secretory pathway 12 N-linked and 10 O-linked carbohydrate side chains are added. Importantly, VWF dimers are multimerized via N-terminal disulfide bridges and the propeptide of 741 amino acids is cleaved off by the enzyme PACE/furin in the late Golgi apparatus. The propeptide as well as the high-molecular-weight multimers of VWF (VWF-HMWM) are stored in the Weibel-Pallade bodies of endothelial cells or in the α-Granules of platelets.

Once secreted into plasma the protease ADAMTS13 cleaves VWF within the A1 domain of VWF. Plasma VWF consists of a range of multimers ranging from single dimers of 500 kDa to multimers consisting of more than 20 dimers of a molecular weight of over 10,000 kDa. Typically VWF high molecular weight multimers (VWF-HMWM) have the strongest hemostatic activity, which can be measured in ristocetin cofactor activity (VWF:RCo). The higher the ratio of VWF:RCo/VWF antigen, the higher the relative amount of high molecular weight multimers.

Defects in VWF are causal to von Willebrand disease (VWD), which is characterized by a more or less pronounced bleeding phenotype. VWD type 3 is the most severe form in which VWF is completely missing, VWD type 1 relates to a quantitative loss of VWF and its phenotype can be very mild. VWD type 2 relates to qualitative defects of VWF and can be as severe as VWD type 3. VWD type 2 has many sub forms some of them being associated with the loss or the decrease of high molecular weight multimers. VWD type 2a is characterized by a loss of both intermediate and large multimers. VWD type 2B is characterized by a loss of highest-molecular-weight multimers.

VWD is the most frequent inherited bleeding disorder in humans and can be treated by replacement therapy with concentrates containing VWF of plasma or recombinant origin. VWF can be prepared from human plasma as for example described in EP 05503991. EP 0784632 describes a method for producing and isolating recombinant VWF.

The method of purifying VWF described in EP 0784632 involves anion exchange chromatography followed by affinity chromatography. A simpler and less complex purification protocol would be beneficial, particularly one in which the VWF is recovered in the flow through liquid and does not require elution from a resin.

Additionally, VWF can undergo conformational changes under pressure, which can quickly lead to column blockage using conventional chromatography methods such as described in EP 05503991 and EP 0784632. The VWF purification methods of the present invention are relatively less prone to column blockage.

SUMMARY OF THE INVENTION

The present invention provides a method of purifying multimeric von Willebrand Factor (VWF) from a solution comprising multimeric VWF and contaminants, the method comprising passing the solution through a chromatography column comprising beads of a mixed mode chromatography resin coated with a size-exclusion inactive shell and collecting the multimeric VWF which passes through the column without binding to the resin.

The present invention also provides multimeric VWF preparations produced by the method of the present invention.

DETAILED DESCRIPTION

Figure 1:
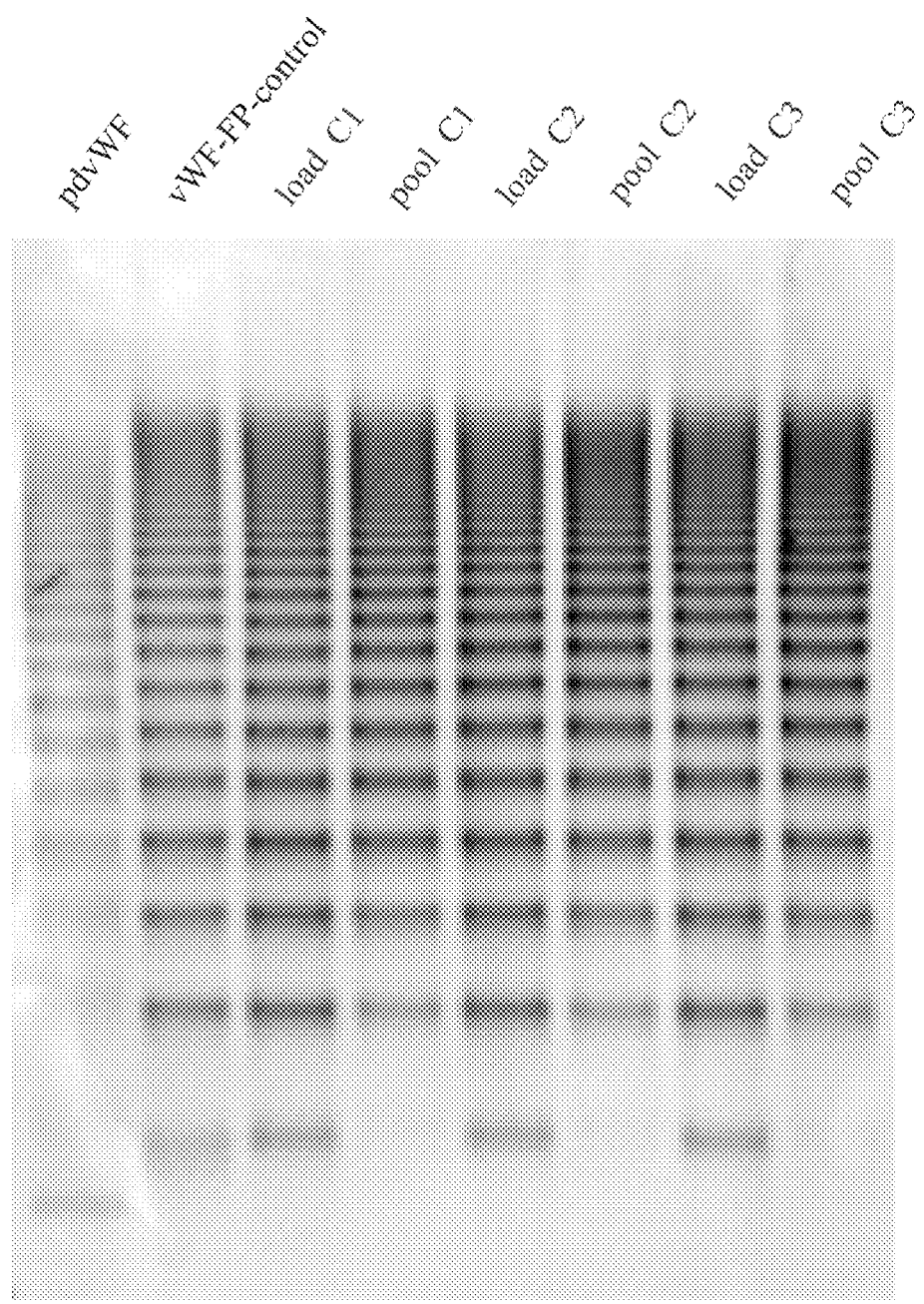
FIG. 1 shows an image of a Western blot showing the VWF multimer pattern of the load material (load C1, load C2 and load C3) prior to loading a Capto™ Core 700 column and the multimer pattern (substantially devoid of dimer) of the VWF recovered from the Capto™ Core 700 column (pool C1, pool C2 and pool C3). pdWF means plasma-derived VWF.

The present invention provides an efficient method of separating VWF from lower molecular weight contaminants by use of chromatography using beads of a mixed mode chromatography resin coated with a size-exclusion inactive shell.

The mixed mode chromatography resin comprises ligands capable of multiple modes of interaction. For example, the resin may comprise ligands that are both hydrophobic and either positively or negatively charged. In one embodiment of the invention, the mixed mode resin comprises a ligand that is both hydrophobic and positively charged. Other mixed mode resins are also contemplated by the current invention e.g. hydrophobic, anionic ligands with hydrogen bonding, mixed-mode cationic ligands with hydrophobic binding and mixed-mode pH-controllable sorbents. The mixed mode resin should be capable of binding most, or preferably substantially all of the contaminants which are able to enter the bead.

Contaminants include various molecules including nucleic acids, lipids, proteins, endotoxin, other molecules and fragments and/or derivatives thereof. When the method of the present invention is used to purify VWF from plasma, e.g. human plasma, contaminants would likely include other plasma proteins and fragments thereof, for example FVIII. When the method of the present invention is used to purify recombinant VWF, the contaminants will likely include host cell nucleic acids and host cell proteins derived from the cells used to express the recombinant VWF (e.g. CHO cells) and cell culture media-derived elements.

The size-exclusion inactive shell provides a barrier to the mixed mode chromatography resin preventing larger molecular molecules or particles (e.g. viruses) from entering the bead and interacting with the resin. The size-exclusion inactive shell preferably comprises agarose or similar material. It is preferred that the molecular weight cut-off of the size-exclusion inactive shell is about 700 kDa.

A preferred example of the beads of the mixed mode chromatography resin coated with a size-exclusion inactive shell is the product sold by GE Healthcare Life Sciences under the name Capto™ Core 700. The mixed mode chromatography resin of Capto™ Core 700 comprises octylamine ligands which are both hydrophobic and positively charged. This enables the efficient binding of contaminants which enter the bead. The size-exclusion inactive shell of Capto™ Core 700 comprises highly cross-linked agarose.

Further details regarding this material can be found at WO2009/131526, the disclosure of which is included herein by cross-reference. Previously known applications of this material include virus purification, including the purification of influenza virus and human papilloma virus.

In a preferred embodiment of the present invention the VWF is recombinant VWF and the contaminants are proteins derived from the host cells expressing the recombinant VWF and/or compounds derived from cell culture media. It is further preferred that the recombinant VWF is a VWF fusion protein (VWF-FP) in which it is preferred that the VWF is linked to human serum albumin as described in Schulte et al (2013), Thrombosis Research 131, (Supplement 2) 2-6, the disclosure of which is incorporated herein by cross reference.

Recombinant VWF includes functional variants that are capable of multimerising and which retain one or more properties of VWF (e.g. variants such as those described in WO2009/156137, WO2011/060242, WO2013/083858 and WO2013/106787). Recombinant VWF fusion proteins include fusions with albumin or albumin derivatives, and other molecules designed to increase plasma half-life of VWF such as PEG or an Fc moiety of a human immunoglobulin molecule.

In a further embodiment the method of the present invention, dimeric VWF is retained by the mixed-mode resin such that the level of dimeric VWF remaining in the multimeric VWF which flows through the column is reduced by at least about 80%.

Preferably the level of dimeric VWF is reduced by at least about 85%, at least 90%, at least about 91%, at least about 92%, at least about 93%, at least about 94%, at least about 95%, at least about 96%, at least about 97%, at least about 98% or at least about 99%.

The present inventor has also found that by appropriate adjustment of conditions, the method of the present invention can be used to remove VWF propeptide (VWFpp) present in the solution of recombinant multimeric VWF.

Preferably the level of VWFpp is reduced by at least about 80%, at least about 85%, at least about 90%, at least about 91%, at least about 92%, at least about 93%, at least about 94%, at least about 95%, at least about 96%, at least about 97%, at least about 98% or at least about 99%.

In a still further preferred the embodiment the solution comprising recombinant multimeric VWF is passed through the column in the presence of EDTA preferably at a concentration of about 10 mM. It is also preferred that multimeric VWF is passed through the column at substantially neutral pH, that is a pH of about 7.0.

One advantage of the present method is that binding of contaminants to the mixed mode resin is possible across a broad range of salt concentrations and pH values. Accordingly, the load material can be an eluate from a different chromatography column comprising, for example, a high salt concentration required for elution of bound material. Thus it may be possible to exclude a step of adjusting the salt concentration and/or pH of the load material to maintain high performance of the present method. The present method may also be adaptable for loading cell culture material directly without any need for a preliminary purification step, e.g. ion exchange chromatography or affinity chromatography.

It is preferred that the salt concentration is less than about 1M NaCl, preferably between about 50 mM and about 800 mM, preferably between about 100 mM and about 500 mM and preferably about 400 mM.

Preferably the pH is between about 3.0 and about 13.0, preferably between about 4.0 and about 9.0 and preferably about 5.0 to about 8.0. It is preferably preferred that the method operates with high protein loads and preferably a load of about 50 to about 500 IU/ml of VWF, preferably about 100 to about 400 IU/ml, preferably about 200 to about 300 IU/ml.

The present inventor also found that purification of recombinant VWF multimers in accordance with the present invention was possible using various concentrations of loading material.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The disclosures of all references referred to in this application are included herein by cross-reference.

In order that the present invention may be more clearly understood preferred forms thereof will now be described by reference to the following Examples.

Example 1

High throughput process development screens in a batch 96-well format with Capto™ Core 700 were performed investigating the effects of load recombinant VWF-FP (recombinant VWF fused to recombinant HAS) (100-400 IU/mL), pH (5.5-6.25) and NaCl (100-500 mM) on product yield, quality and host cell protein (HCP) removal. No significant changes to the multimer content were found across all investigated conditions. The method was successfully scaled up 20-fold.

Example 2

A solution comprising recombinant VWF-FP (recombinant VWF fused to recombinant HAS) and host cell protein contaminants was applied to a column packed with Capto™ Core 700. The bed height was 12.5 cm with a flowrate giving 6 min residence time. The load target was 200 IU/mL and the process was conducted using as a buffer 50 mM MES, 400 mM NaCl, pH 5.75.

No column blockage was observed during the run and the process removed VWF dimer with a consequent increase in VWF:RCoNWF:Ag. The yield of the process approached 100% for VWF:RCo with substantial host cell protein removal (down to 1000-3000 ppm). As shown in FIG. 1, when comparing load material with flow through material, there was essentially an unchanged multimer pattern with the exception of the dimer which was removed during the process.

Example 3

The method was also investigated for removal of VWF propeptide (VWFpp). It was found that by addition of 10 mM EDTA, adjustment of the pH to about 7.0, load target reduction to 100 IU/mL and a residence time of 12 min that the column could be run without blockage with VWFpp removal.

Example 4

The ability of Capto™ Core 700 to remove VWF propeptide in the presence or absence of EDTA was assessed over a range of pH values using a high throughput process development screen in batch 96-well form. The results obtained are shown in FIG. 2.

In this series of small scale experiments, solutions comprising recombinant VWF-FP (recombinant VWF fused to recombinant human serum albumin) and host cell protein contaminants were applied to Capto™ Core 700 resin. The load target was 200 IU/mL and the load buffer comprised 50 mM MES, 500 mM NaCl with or without EDTA (10 mM).

Figure 2:
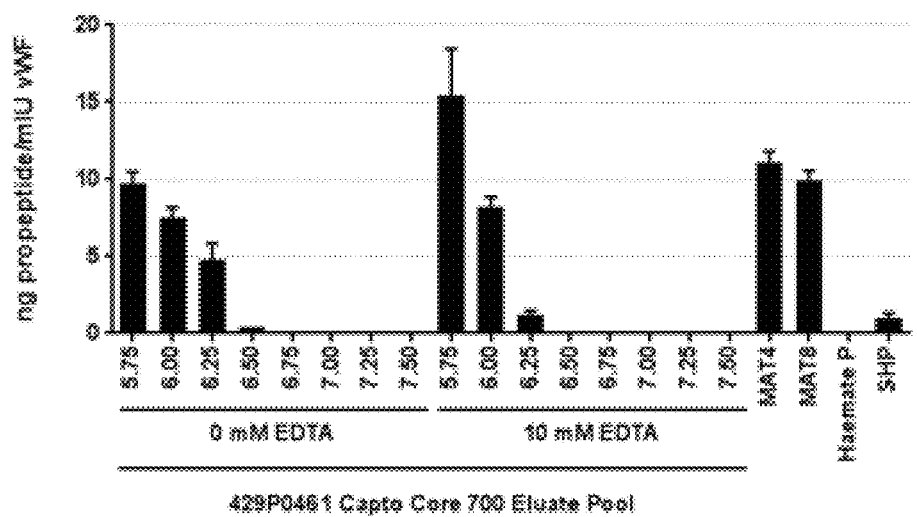
FIG. 2 shows a graphical representation of the amount of VWF propeptide (ng/mIU) recovered from the flow through eluates of Capto™ Core 700 resin. Resins were loaded with solutions, comprising recombinant VWF-FP and host cell protein contaminants, having a range of pH values and having either no EDTA or 10 mM EDTA. VWF propeptide was also measured in the following control samples that were not applied to Capto™ Core 700 resin: MAT-4 and MAT-5 pilot scale batches of recombinant VWF-FP known to comprise VWF propeptide; SHP—standard human plasma; and HaemateP—a commercial batch of plasma-derived human coagulation factor VIII.

As can be seen from FIG. 2, significant reduction, up to complete removal, of VWF propeptide was achieved at pH values of 6.50 and above, in the presence or absence of 10 mM EDTA.

Example 5

A series of experiments was conducted using 10 mM EDTA at various pH values. The results are set out in Table 1.

In this series of experiments, solutions containing VWF-FP (recombinant VWF fused to recombinant human serum albumin), and host cell protein contaminants were applied to columns packed with Capto™ Core 700. The load target was 200 IU/mL and the load buffer comprised 50 mM MES and 500 mM NaCl, with or without EDTA (10 mM). The column diameter was 1.1 cm, bed height was 10 cm and the residence time was 12 min.

As can be seen from the results set out in Table 1, a high yield of VWF-FP was obtained using Capto™ Core 700 resin across a range of pH values.

TABLE 1

| Condition | Yield (VWF:Ag) | Yield (VWF:RCo) | Ratio of VWF:RCo/VWF:Ag | HCP/VWF:Ag [ppm] | VWFpp [ng/mIU] |
|---|---|---|---|---|---|
| pH 5.75 0 mM EDTA | 78.0 | 101.3 | 1.30 | 1,124 | 8.42 ± 0.15 |
| pH 6.25 10 mM EDTA | 75.0 | 88.7 | 1.36 | 1,080 | 3.39 ± 0.17 |
| pH 6.5 10 mM EDTA | 70.7 | 81.4 | 1.29 | 907 | 0.23 ± 0.01 |
| pH 6.5 10 mM EDTA (Repeat) | 73.0 | 94.0 | 1.33 | 1,147 | <LOD |

LOD = limit of detection; Yield (VWF:Ag) = Percentage recovery of VWF-FP as calculated by measurement of VWF antigen; Yield (VWF:RCo) = Percentage recovery of VWF-FP as calculated by measurement of ristocetin cofactor activity; HCP/Ag (ppm) = the quantity of host cell protein contaminants expressed as parts per million parts of protein content equivalent to VWF antigen content; VWFpp (ng/mIU) = the quantity of VWF propeptide expressed in ng per milli-International Units of VWF.

The invention claimed is:

1. A method of purifying multimeric von Willebrand Factor (VWF) from a solution comprising recombinant multimeric VWF and contaminants, the method comprising passing the solution through a chromatography column comprising beads of a mixed mode chromatography resin coated with a size-exclusion inactive shell and collecting the recombinant multimeric VWF which passes through the column without binding to the resin and without blocking the resin, wherein the contaminants are proteins derived from the host cells expressing the recombinant multimeric VWF, and wherein dimeric VWF is retained by the resin such that the level of dimeric VWF present in the multimeric VWF which passes through the column is reduced by at least about 80%.

2. The method according to claim 1 wherein the mixed mode chromatography resin comprises ligands capable of multiple modes of interaction.

3. The method according to claim 1 wherein the resin comprises ligands that are both hydrophobic and positively charged.

4. The method according to claim 1 wherein the molecular weight cut-off of the size-exclusion inactive shell is about 700 kDa.

5. The method according to claim 1 wherein the beads of the mixed mode chromatography resin coated with a size-exclusion inactive shell is Capto™ Core 700.

6. The method according to claim 1 wherein the recombinant VWF is a VWF fusion protein.

7. The method according to claim 1 wherein the method removes VWF propeptide present in the solution of recombinant multimeric VWF.

8. The method according to claim 7 wherein the solution comprising recombinant multimeric VWF is passed through the column in the presence of EDTA.

9. The method according to claim 8 wherein the concentration of EDTA is about 10 mM.

10. The method according to claim 7 wherein the solution comprising recombinant multimeric VWF is passed through the column at a pH of about 6.5 to about 7.5.

\* \* \* \* \*